(12) United States Patent
Quan et al.

(10) Patent No.: US 10,889,408 B2
(45) Date of Patent: Jan. 12, 2021

(54) MICRONEEDLE PATCH STORAGE TOOL, LOWER PALLET AND UPPER PALLET

(71) Applicant: COSMED PHARMACEUTICAL CO., LTD., Kyoto (JP)

(72) Inventors: Ying-Shu Quan, Kyoto (JP); Ying-Zhe Li, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 0 days.

(21) Appl. No.: 15/780,996

(22) PCT Filed: Oct. 6, 2016

(86) PCT No.: PCT/JP2016/079800
§ 371 (c)(1),
(2) Date: Jun. 1, 2018

(87) PCT Pub. No.: WO2017/094352
PCT Pub. Date: Jun. 8, 2017

(65) Prior Publication Data
US 2019/0283933 A1    Sep. 19, 2019

(30) Foreign Application Priority Data

Dec. 4, 2015  (JP) ................. 2015-237381

(51) Int. Cl.
*B65D 19/44*    (2006.01)
*A61M 37/00*    (2006.01)
(Continued)

(52) U.S. Cl.
CPC ............. *B65D 19/44* (2013.01); *A61M 37/00* (2013.01); *A61M 37/0015* (2013.01);
(Continued)

(58) Field of Classification Search
CPC .......... A61M 37/0015; A61M 2209/06; B65D 19/44; B65D 19/0002; B65D 85/00;
(Continued)

(56) References Cited

U.S. PATENT DOCUMENTS 5,492,223 A * 2/1996 Boardman ........ H01L 21/67333
206/509
5,794,783 A * 8/1998 Carter ............... H01L 21/67333
206/562
(Continued)

FOREIGN PATENT DOCUMENTS

CN   101548373 A    9/2009
CN   103796710 A    5/2014
(Continued)

OTHER PUBLICATIONS

Extended European Search Report for European Application No. 16870292.6, dated Jul. 8, 2019.
(Continued)

*Primary Examiner* — Chun Hoi Cheung
(74) *Attorney, Agent, or Firm* — Birch, Stewart, Kolasch & Birch, LLP

(57) ABSTRACT

To suppress the work cost for the washing of the microneedle and the application of the medicament.
A microneedle patch storage tool according to one aspect of the present invention is a microneedle patch storage tool for storing a microneedle patch and comprises a plurality of pallets stacked in a vertical direction, and the two pallets adjacent in the vertical direction constitute one or a plurality of patch holding parts for holding the microneedle patch, and the patch holding part comprises a plurality of lower protrusions arranged in circumferentially divided manner so as to sandwich a peripheral edge part of the microneedle patch in the vertical direction and supporting the peripheral edge part of the microneedle patch from a lower side and a (Continued)

plurality of upper protrusions arranged in circumferentially divided manner and pressing the peripheral edge part of the microneedle patch from an upper side and is opened to at least one of upper and lower directions.

7 Claims, 10 Drawing Sheets

(51) Int. Cl.
  *B65D 19/00* (2006.01)
  *B65D 85/00* (2006.01)
(52) U.S. Cl.
  CPC ......... *B65D 19/0002* (2013.01); *B65D 85/00* (2013.01); *A61M 2209/06* (2013.01); *B65D 2519/00034* (2013.01); *B65D 2519/00069* (2013.01); *B65D 2519/00268* (2013.01); *B65D 2519/00815* (2013.01); *B65D 2519/00965* (2013.01)
(58) Field of Classification Search
  CPC ........... B65D 2519/00034; B65D 2519/00069; B65D 2519/00268; B65D 2519/00815; B65D 2519/00965
  USPC .......................................... 206/438, 710–728
  See application file for complete search history.

(56) References Cited

U.S. PATENT DOCUMENTS

| 5,988,394 | A | * | 11/1999 | Emoto | ............... | B65D 21/0204 |
| | | | | | | 206/562 |
| 7,410,060 | B2 | * | 8/2008 | Crisp | ................ | H01L 21/67333 |
| | | | | | | 206/564 |
| 8,937,483 | B2 | * | 1/2015 | Jeong | ................ | H01L 21/67333 |
| | | | | | | 324/537 |
| 2005/0269242 | A1 | * | 12/2005 | Crisp | ................ | H01L 21/67333 |
| | | | | | | 206/710 |
| 2008/0173569 | A1 | * | 7/2008 | Forsyth | ............. | H01L 21/67333 |
| | | | | | | 206/725 |
| 2010/0256568 | A1 | * | 10/2010 | Frederickson | .... | A61M 37/0015 |
| | | | | | | 604/173 |
| 2012/0043253 | A1 | * | 2/2012 | Jeong | ................ | H01L 21/67333 |
| | | | | | | 206/710 |
| 2013/0218084 | A1 | | 8/2013 | Tamaru et al. | | |
| 2014/0339117 | A1 | | 11/2014 | Quan et al. | | |
| 2015/0238433 | A1 | | 8/2015 | Yeung et al. | | |
| 2016/0235958 | A1 | | 8/2016 | Quan et al. | | |
| 2016/0354591 | A1 | | 12/2016 | Ueno | | |

FOREIGN PATENT DOCUMENTS

| JP | 2011-140339 A | 7/2011 |
| JP | 3152532 U | 7/2011 |
| JP | 2015-61677 A | 4/2015 |
| JP | 2015-83503 A | 4/2015 |
| WO | WO 2015/040697 A1 | 3/2015 |
| WO | WO 2015/129894 A1 | 9/2015 |

OTHER PUBLICATIONS

International Search Report for PCT/JP2016/079800 (PCT/ISA/210) dated Dec. 27, 2016.
Written Opinion of the international Searching Authority for PCT/JP2016/079600 (PCT/ISA/237) dated Dec. 27, 2016.
Japanese Office Action dated Aug. 20, 2019, for Japanese Patent Application No. 2015-237381, with English translation.
Chinese Office Action and Search Report dated Jul. 13, 2020, for Chinese Application No. 201680070983.3, with partial English translation.

* cited by examiner

[Fig 1]
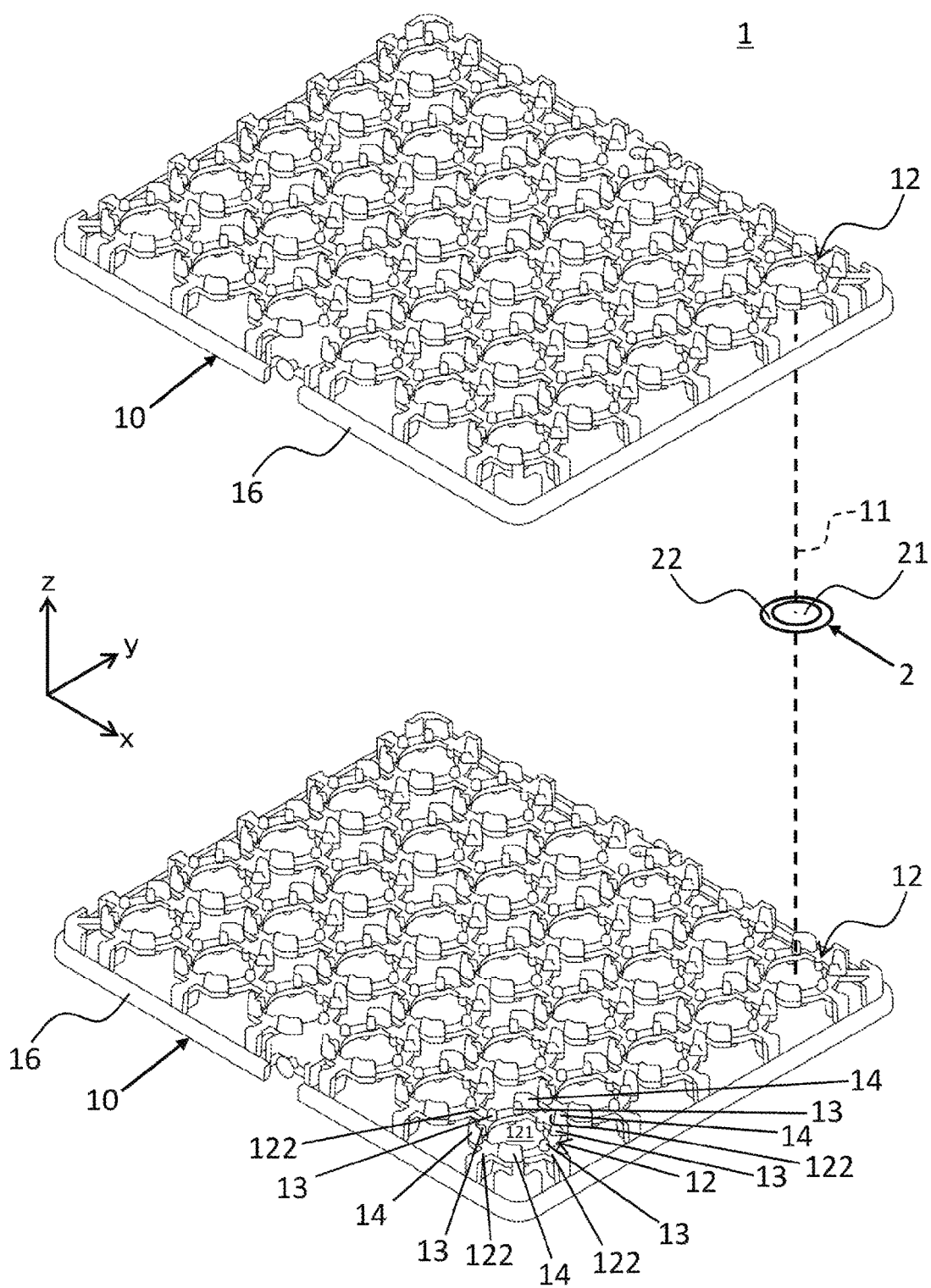

[Fig 2]
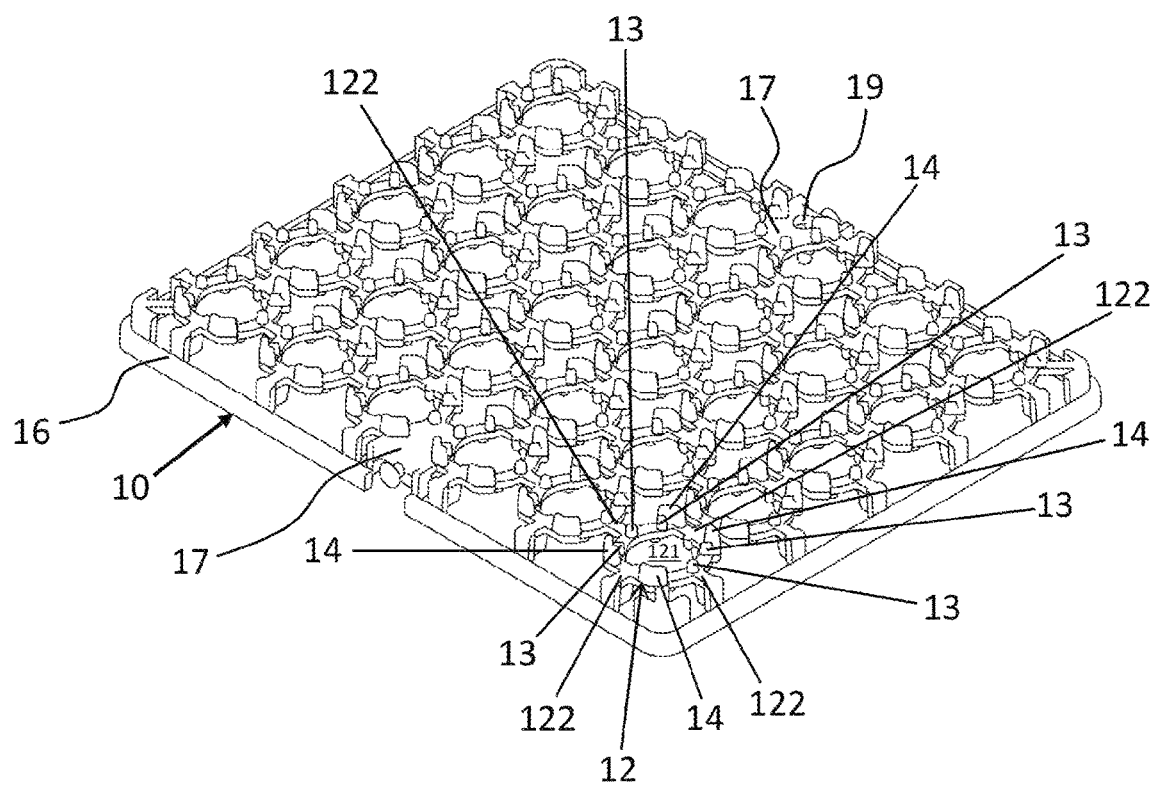

[Fig 3]
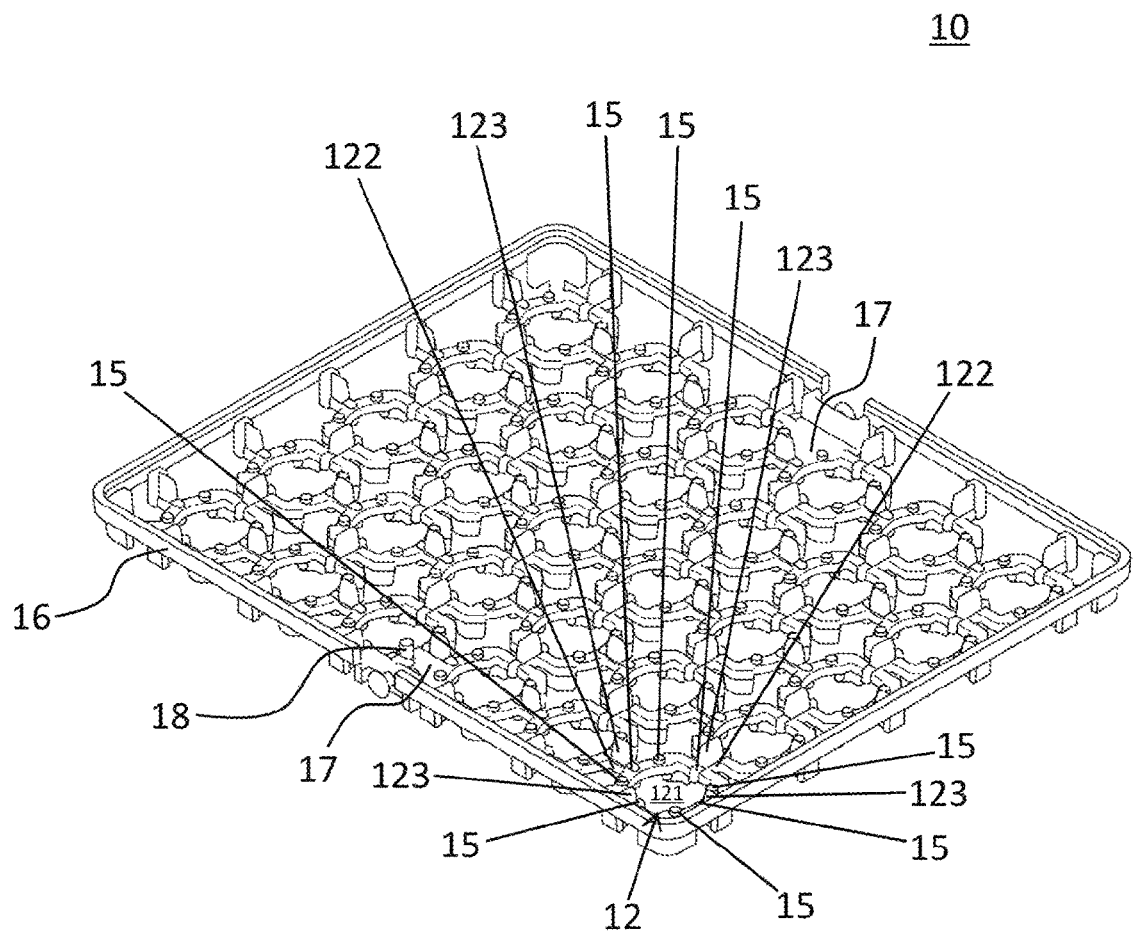
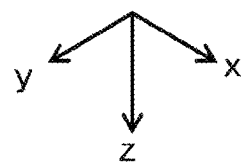

[Fig 4]
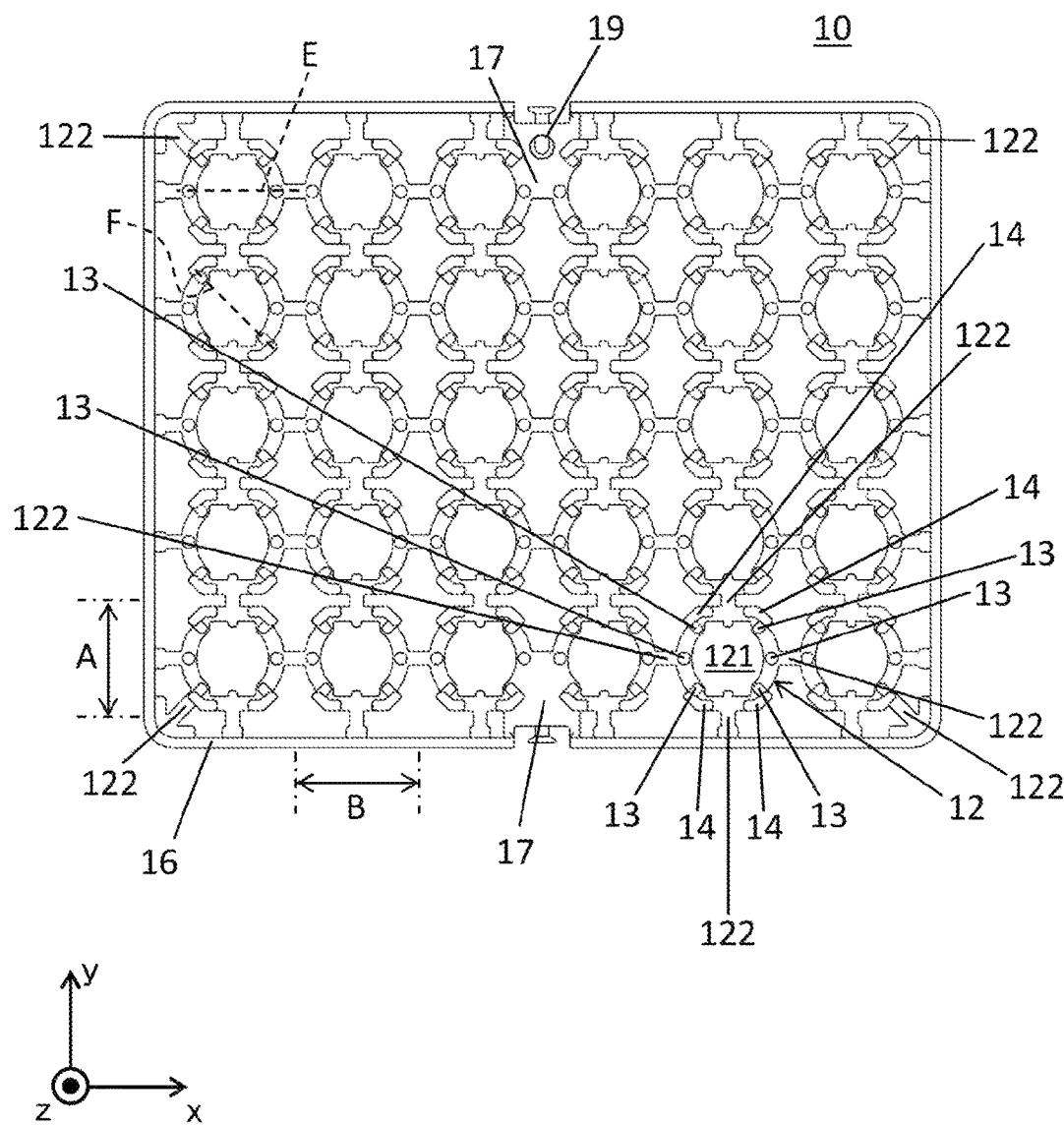

[Fig 5]
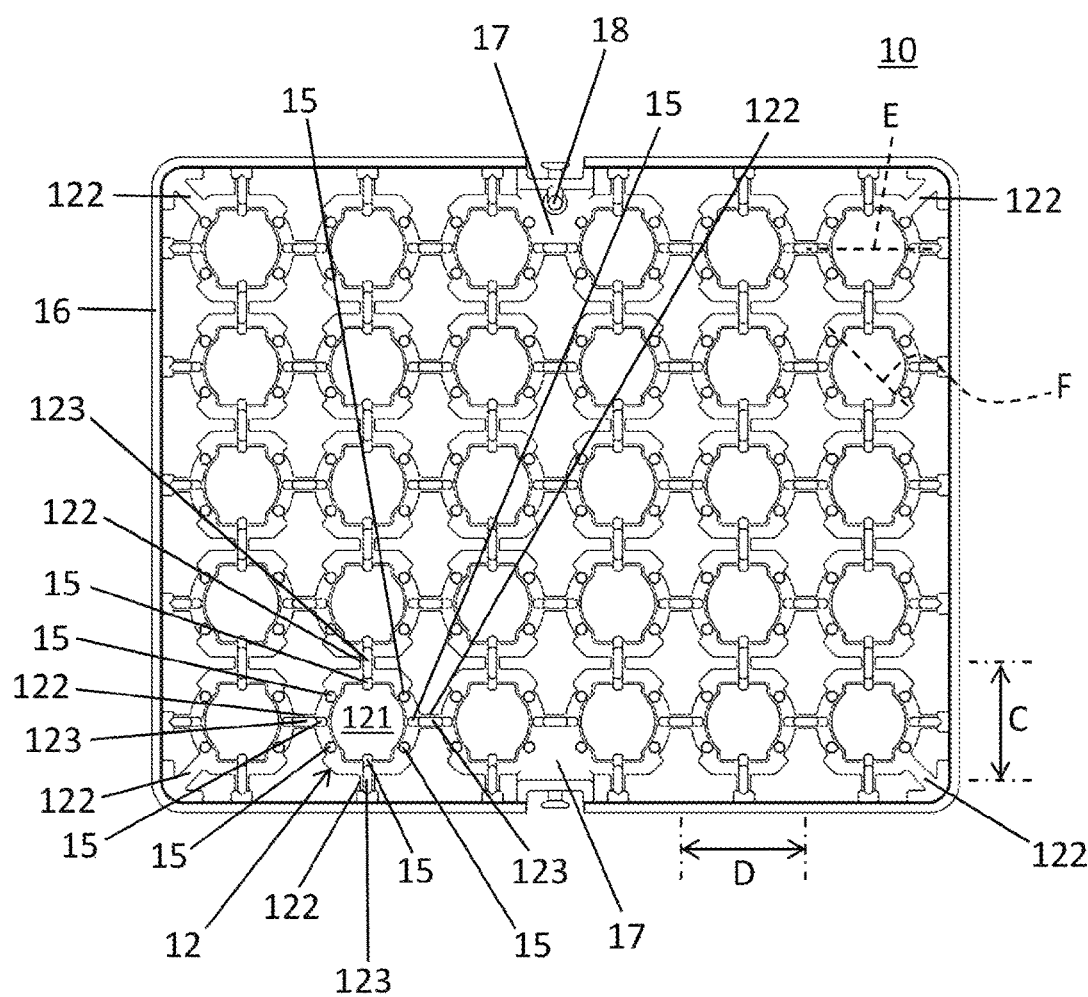

[Fig 6]
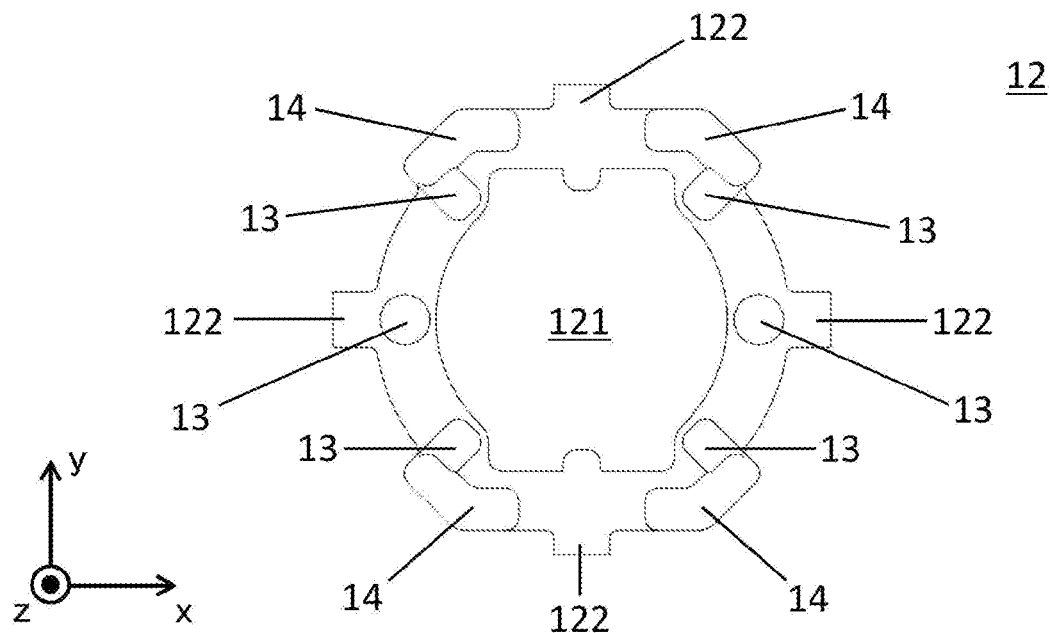
[Fig 7]
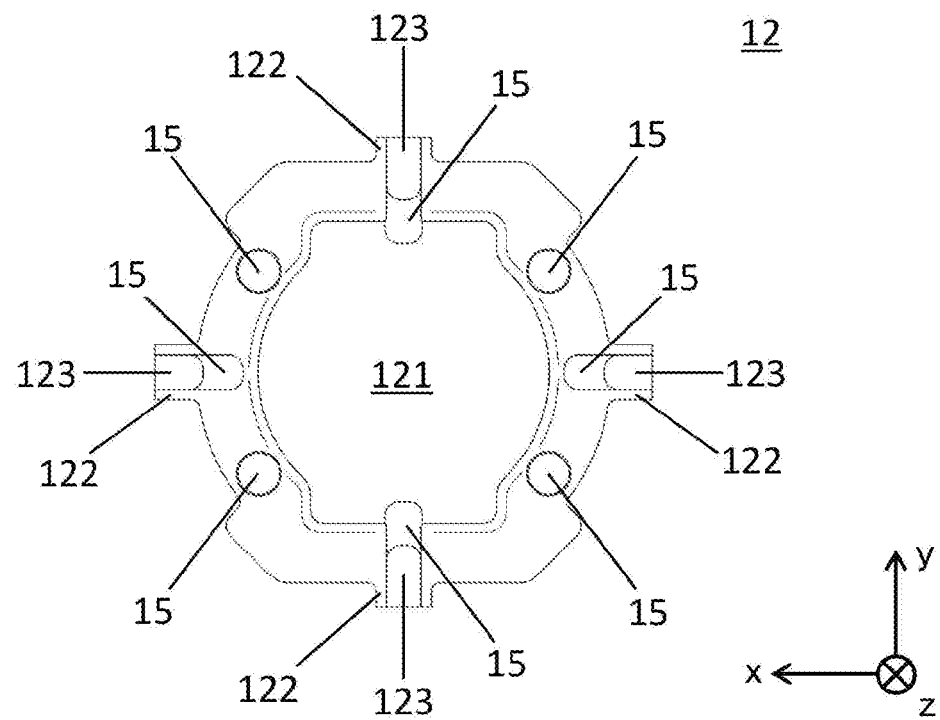

[Fig 8]
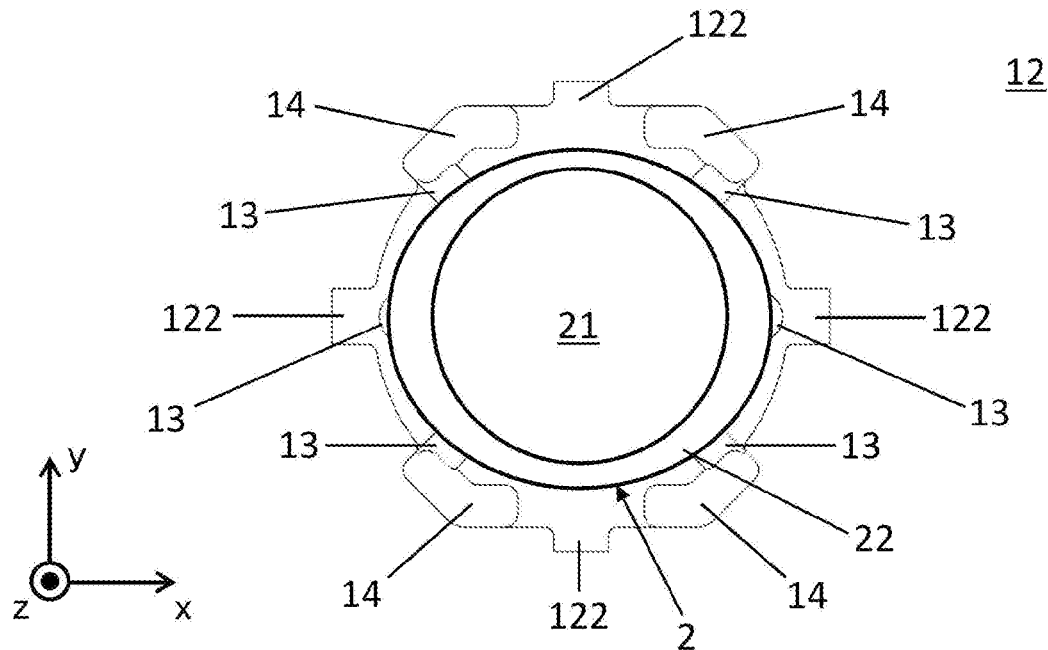
[Fig 9]
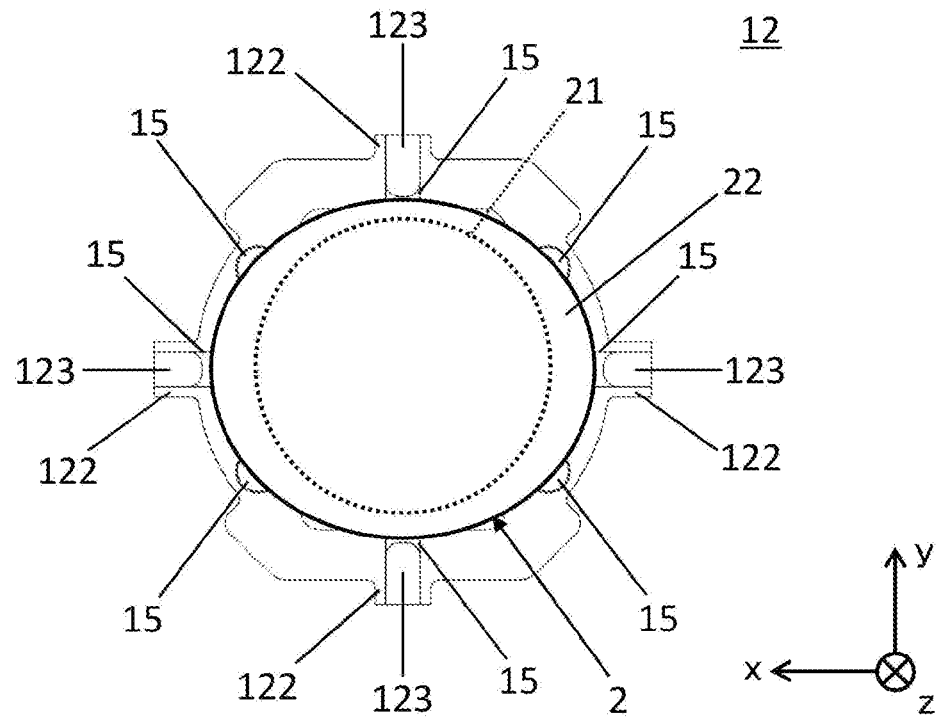

[Fig 10]
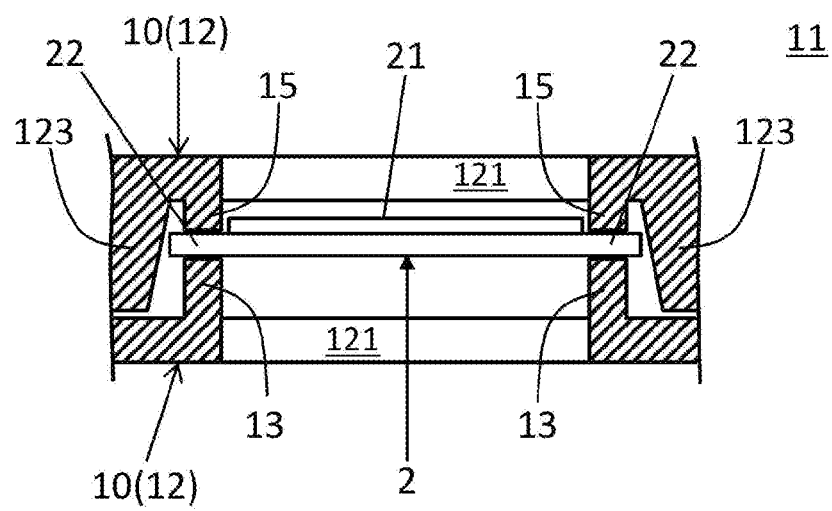
[Fig 11]
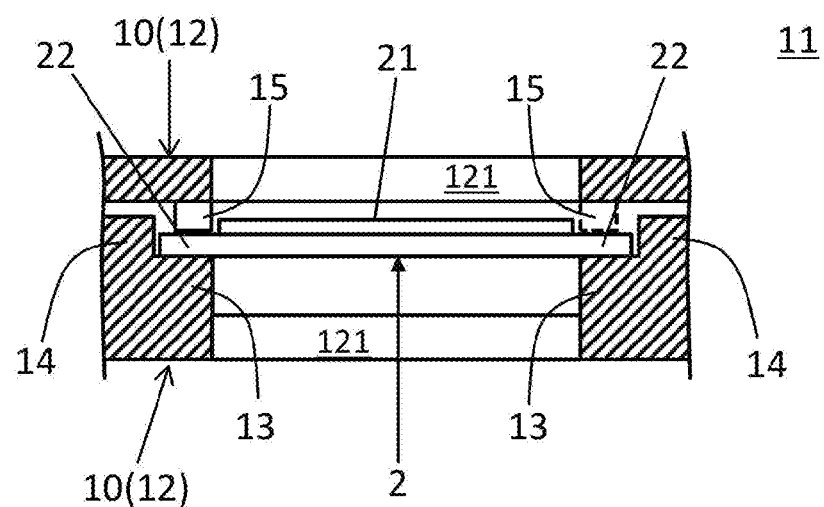

[Fig 12]
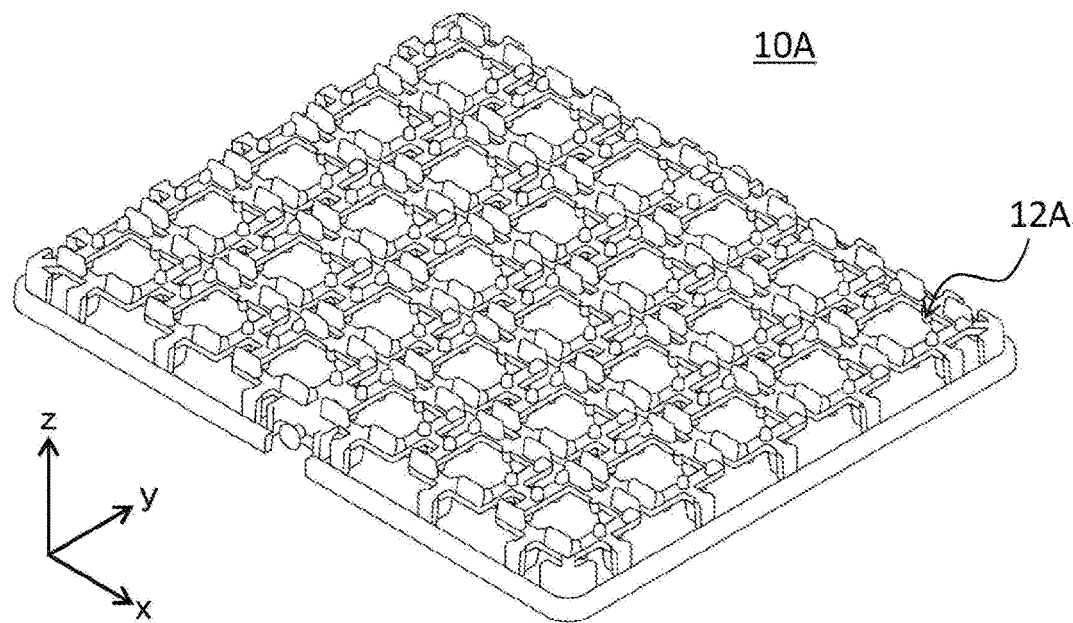
[Fig 13]
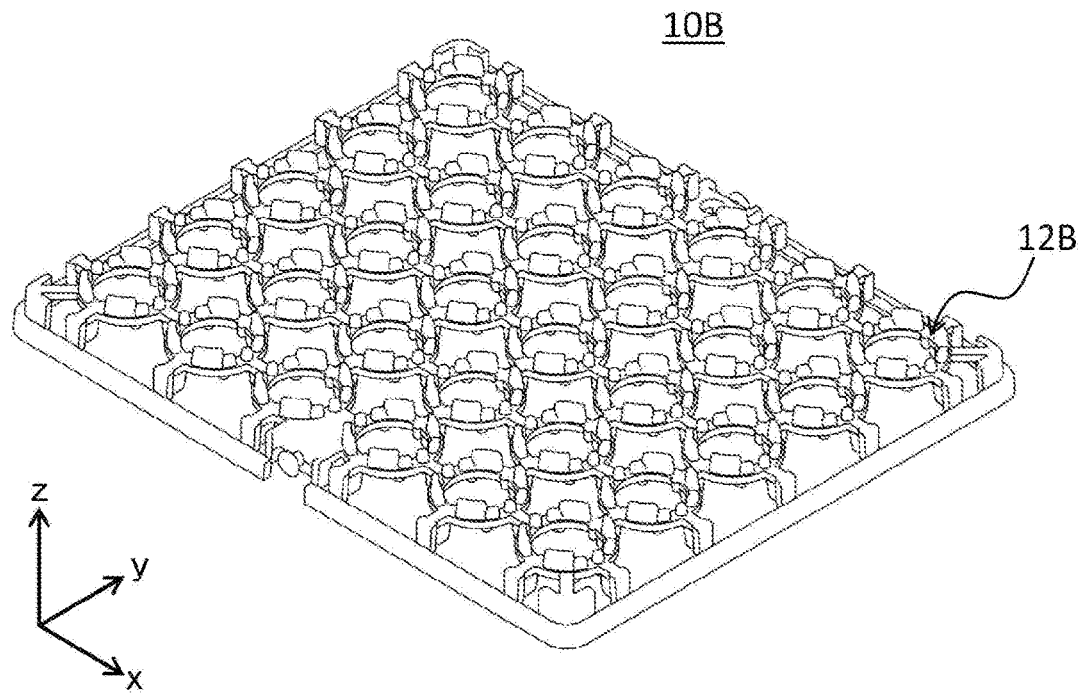

[Fig 14]
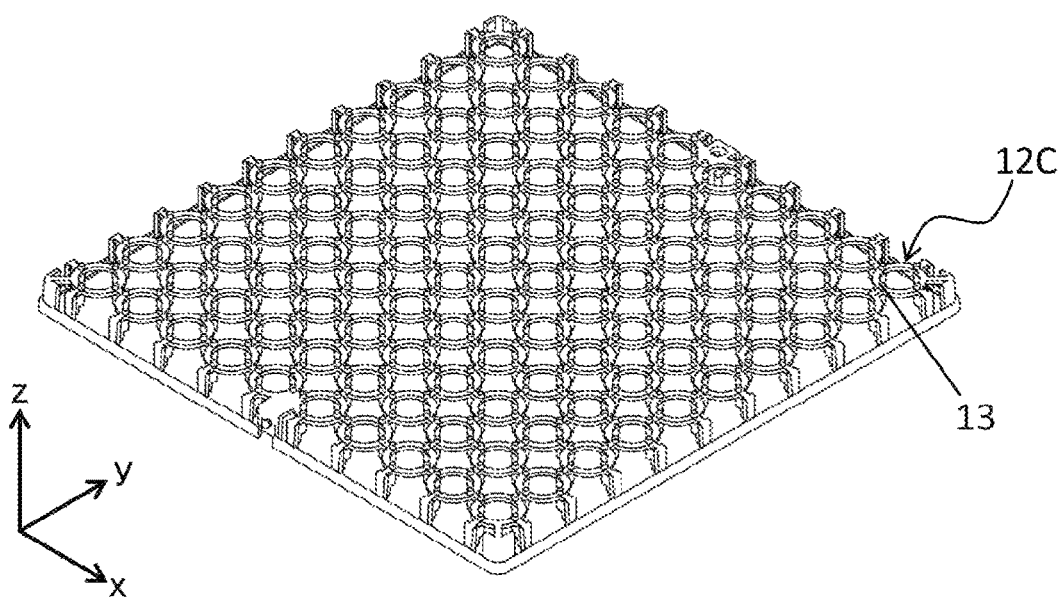

MICRONEEDLE PATCH STORAGE TOOL, LOWER PALLET AND UPPER PALLET

TECHNICAL FIELD

The present invention relates to a technology of a microneedle patch storage tool, a lower pallet and an upper pallet.

BACKGROUND ART

In recent years, a microneedle technology in which a medicament is impregnated in a surface a fine needle of a micro unit or inside of the needle, and the needle is applied on a skin so as to introduce the medicament into the body has been developed. According to this microneedle technology, the medicament can be introduced into the body without accompanying a pain as in the case of injection. This microneedle technology is used for delivering hyaluronic acid and collagen into a deep portion in keratin in the cosmetics field, for example.

This microneedle can be classified into two types by a material constituting the needle, that is, a soluble type and a non-soluble type. In the soluble type microneedle, the needle is constituted by the medicament to be introduced into the body such as hyaluronic acid, collagen and the like. Thus, according to this soluble type microneedle, since the needle (microneedle) is dissolved in the skin, the medicament contained in the needle can be introduced into the body. In Patent Literatures 1 and 2, a storage tool storing a patch comprising this soluble type microneedle is proposed. Hereinafter, the patch comprising the microneedle is referred to also as a "microneedle patch".

On the other hand, in the non-soluble type microneedle, the needle is constituted by biodegradable polymer such as PGA (polyglycol acid), PLA (polylactic acid) and the like, and the medicament to be introduced into the body is applied on a tip end portion of the needle. Thus, according to this non-soluble type microneedle, by introducing the needle constituted by the biodegradable polymer into the body, the medicament applied on the tip end portion of the needle can be introduced into the body.

In the soluble type microneedle, the needle itself is constituted by the medicament, while in the non-soluble type microneedle, the medicament is applied on the tip end portion of the needle introduced into the body. Thus, as compared with the soluble type microneedle, according to the non-soluble type microneedle, an amount of the medicament not introduced into the body can be reduced, whereby the medicament can be utilized efficiently.

Moreover, once the soluble type microneedle is used for administering the medicament, it cannot be basically used for administering the medicament again. On the contrary, the non-soluble type microneedle can be used for administering the medicament again by washing the needle and by applying the medicament on the tip end portion of the needle after it is used once for administering the medicament. That is, the non-soluble type microneedle has high reusability. Thus, the non-soluble type microneedle has attracted attention in recent years rather than the soluble type microneedle.

CITATION LIST

Patent Literature

[Patent Literature 1] Japanese Patent Laid-Open No. 2015-061677

[Patent Literature 2] Japanese Patent Laid-Open No. 2015-083503

SUMMARY OF THE INVENTION

Technical Problem

Regarding the soluble type microneedle patch, since the needle is constituted by the medicament to be introduced into the body, by performing a step of manufacturing the microneedle, a step of loading the medicament on the tip end portion of the needle is performed at the same time. That is, the step of manufacturing the microneedle cannot be separated from the step of loading the medicament on the tip end portion of the needle. Thus, this soluble type microneedle patch is stored in a storage tool exemplified in Patent Literatures 1 and 2 so that its medical efficacy is not lost and the medicament is not contaminated after the microneedle is manufactured. The soluble type microneedle patch is preferably sealed in the storage tool after the manufacture.

On the other hand, regarding the non-soluble type microneedle patch, after the needle (hereinafter described also as a "microneedle") is manufactured by biodegradable polymer, the medicament to be introduced into the body is applied on the tip end portion of the needle in another step. That is, the step of manufacturing the microneedle can be separated from the step of loading the medicament on the tip end portion of the needle. Thus, after the microneedle patch is manufactured in a plant, the manufactured microneedle patch can be transported to another place such as another plant or the like, and the washing of the microneedle and application of the medicament can be carried out at the another place, for example.

However, for the transportation to another place, the manufactured microneedle is stored in the storage tool once. Then, if the storage tool for the soluble type microneedle patch exemplified in Patent Literatures 1 and 2 is used in order to transport the manufactured microneedle, the following problems occur.

That is, since such a usage is not assumed for the storage tool for the soluble type microneedle patch, the microneedle patch is basically stored so as not to be exposed to the outside. Thus, after the microneedle patch is stored in the storage tool, washing of the microneedle and application of the medicament cannot be carried out unless the microneedle patch is taken out of the storage tool. Therefore, if the storage tool for the soluble type microneedle patch is used for transportation of the non-soluble type microneedle patch, a work cost for the washing of the microneedle and the application of the medicament rises, which is a problem.

The present invention was made by considering such a point in one aspect and has an object to suppress the work cost for the washing of the microneedle and the application of the medicament.

Solution to Problem

The present invention employs the following configuration in order to solve the aforementioned problem.

That is, the microneedle patch storage tool according to one aspect of the present invention is a microneedle patch storage tool for storing a microneedle patch and comprises a plurality of pallets stacked in a vertical direction, and the two pallets adjacent in the vertical direction constitute one or a plurality of patch holding parts for holding the microneedle patch, and the patch holding part comprises a plurality of lower protrusions arranged in circumferentially divided manner so as to sandwich a peripheral edge part of the microneedle patch in the vertical direction and supporting the peripheral edge part of the microneedle patch from a lower side and a plurality of upper protrusions arranged in circumferentially divided manner and pressing the peripheral edge part of the microneedle patch from an upper side and is opened to at least one of upper and lower directions.

In the aforementioned configuration, the microneedle patch storage tool comprises the plurality of pallets stacked in the vertical direction. And the one or the plurality of patch holding parts for holding the microneedle patch is constituted by the two pallets adjacent in the vertical direction in the plurality of pallets stacked in the vertical direction.

This patch holding part is configured to hold the microneedle by sandwiching the peripheral edge part of the microneedle patch from the upper and lower directions by the plurality of lower protrusions and the plurality of upper protrusions arranged in circumferentially divided manner. As a result, the microneedle patch storage tool according to the aforementioned configuration holds the peripheral edge part of the microneedle patch substantially in point contact and thus, the microneedle provided on an inner-plane side of the peripheral edge part can be prevented from being damaged.

In addition, this patch holding part is configured to be opened at least in one of the upper and lower directions. Thus, when the microneedle patch is to be stored in the patch holding part, by directing a surface on which the microneedle is provided toward an open direction of the patch holding part, an access can be made to the microneedle from the outside even after the microneedle patch is stored.

Therefore, in the aforementioned configuration, even in a state where the microneedle patch is stored in the storage tool, the washing of the microneedle and the application of the medicament can be carried out. That is, a step of taking out the microneedle patch from the storage tool before carrying out each of the steps of washing and medicament application can be omitted. Thus, according to the aforementioned configuration, a work cost for the washing of the microneedle and the application of the medicament can be suppressed.

Moreover, as another form of the microneedle patch storage tool according to the one aspect, the patch holding part may be opened to the both upper and lower directions. According to the configuration, an access can be made to the microneedle patch from either of the upper and lower directions. Thus, even in the state where the microneedle patch is stored in the storage tool, an access can be made relatively easily to the microneedle from the outside. Thus, according to the configuration, the steps of the washing of the microneedle and the application of the medicament can be facilitated.

Moreover, as another form of the microneedle patch storage tool according to the one aspect, a plurality of side wall pieces may be provided separately from each other on the patch holding part, and the plurality of side wall pieces may be arranged in circumferentially divided manner so as to surround an outer periphery of the microneedle patch. According to the configuration, since the outer periphery of the microneedle patch can be surrounded by the plurality of side wall pieces, displacement of the microneedle patch stored in the patch holding part can be prevented.

In addition, the plurality of side wall pieces are provided in circumferentially divided manner and separately from each other and thus, the patch holding part is partially opened to a plane direction. Thus, when the microneedle patch is to be washed, a washing liquid can be made to flow in and to flow out also through a region opened to this plane direction in addition to either one of the upper and lower directions. Moreover, when the microneedle patch is to be dried after the microneedle patch is washed, air can be made to flow also through this region opened to the plane direction in addition to either one of the upper and lower directions. Therefore, according to the configuration, the step of the washing and drying of the microneedle patch can be carried out rapidly, whereby the time for the washing and drying step can be made relatively shorter.

Moreover, as another form of the microneedle patch storage tool according to the aforementioned one aspect, the patch holding parts may be provided in plural, the two adjacent patch holding parts may be coupled by a coupling part, and a partition piece for partitioning the two adjacent patch holding parts may be provided on the coupling part. According to the configuration, the plurality of microneedle patches can be stored in the microneedle patch storage tool, and the displacement of the microneedle patch held in each of the patch holding parts can be prevented by the partition piece.

Moreover, as another form of the microneedle patch storage tool according to the aforementioned one aspect, the plurality of patch holding parts may be arranged by being aligned in front-and-rear and in right-and-left. In the configuration, the plurality of microneedle patches stored in the patch holding part is arranged by being aligned in the front-and-rear and in the right-and-left and thus, processing such as the application of the medicament on each of the microneedle patches can be performed relatively easily. Thus, the step of applying the medicament on the tip end portion of each of the microneedles can be performed rapidly, whereby time for the application step can be made relatively shorter.

Moreover, as another form of the microneedle patch storage tool according to the aforementioned one aspect, the plurality of pallets may be formed into the same shape. In the configuration, each pallet is formed into the same shape and thus, there is no more need to manufacture pallets having a plurality of types of shapes. Thus, according to the configuration, a manufacturing cost of the microneedle patch storage tool can be suppressed.

Moreover, as another form of the microneedle patch storage tool according to the aforementioned one aspect, a projection for positioning may be provided on one of the two adjacent pallets, and an insertion hole for accepting the projection may be provided in the other pallet. According to the configuration, when the two adjacent pallets are to be stacked vertically, the two pallets can be aligned by the projection for positioning and the insertion hole. Moreover, after the two pallets are stacked, since the projection for positioning is inserted into the insertion hole, the two pallets are prevented from being displaced. Therefore, according to the configuration, the step of stacking the plurality of pallets can be facilitated, and collapse of the plurality of stacked pallets can be made difficult.

Moreover, as another form of the microneedle patch storage tool according to the aforementioned one aspect, the lower pallet according to the one aspect of the present invention comprises one or a plurality of base parts on each of which the microneedle patch is placed, the base part is formed into a frame shape by providing an opening penetrating in the vertical direction at a center, and on an upper surface of the base part, a plurality of lower protrusions supporting a peripheral edge part of the microneedle patch from a lower side is arranged in circumferentially divided manner. According to the configuration, for the reason similar to the above, the work cost for the washing of the microneedle and the application of the medicament can be suppressed.

Moreover, as another form of the microneedle patch storage tool according to the aforementioned one aspect, the upper pallet according to the aforementioned one aspect of the present invention comprises one or a plurality of base parts covering the placed microneedle patches, the base part is formed into a frame shape by providing an opening penetrating in the vertical direction at a center, and on a lower surface of the base part, a plurality of upper protrusions pressing the peripheral edge part of the microneedle patch from an upper side is arranged in circumferentially divided manner. According to the configuration, for the reason similar to the above, the work cost for the washing of the microneedle and the application of the medicament can be suppressed.

It should be noted that the microneedle patch storage tool of the present invention has a main object of storing the non-soluble type microneedle patch as described above, but it does not exclude the storage of the soluble type microneedle patch. The soluble type microneedle patch and the non-soluble type microneedle patch have substantially the same final shape although their materials and molding methods are different and thus, it is natural that the storage tool for storing a final product can be shared. It is not possible to store the soluble type microneedle patch in the storage tool of the present invention and then, to wash it with water, but in the case of the application of the medicament on the needle tip end of the soluble type microneedle patch, this storage tool functions effectively.

Advantageous Effect of Invention

According to the present invention, the work cost for the washing of the microneedle and the application of the medicament can be suppressed.

BRIEF DESCRIPTION OF DRAWINGS

FIG. 1 is a perspective view exemplifying a microneedle storage tool according to an embodiment.

FIG. 2 is a perspective view exemplifying a pallet according to the embodiment.

FIG. 3 is a rear perspective view exemplifying the pallet according to the embodiment.

FIG. 4 is a plan view exemplifying the pallet according to the embodiment.

FIG. 5 is a bottom view exemplifying the pallet according to the embodiment.

FIG. 6 is an enlarged view of an A-B part in FIG. 4.

FIG. 7 is an enlarged view of a C-D part in FIG. 5.

FIG. 8 is an enlarged view of the A-B part exemplifying a state where the microneedle patch is held.

FIG. 9 is an enlarged view of the C-D part exemplifying the state where the microneedle patch is held.

FIG. 10 is a sectional view related to a line E in FIGS. 4 and 5, schematically exemplifying the state where the microneedle patch is held.

FIG. 11 is a sectional view related to a line F in FIGS. 4 and 5, schematically exemplifying the state where the microneedle patch is held.

FIG. 12 is a perspective view schematically exemplifying a pallet constituting the microneedle storage tool according to another embodiment.

FIG. 13 is a perspective view schematically exemplifying a pallet constituting the microneedle storage tool according to another embodiment.

FIG. 14 is a perspective view schematically exemplifying a pallet constituting the microneedle storage tool according to another embodiment.

DESCRIPTION OF EMBODIMENTS

An embodiment according to one aspect of the present invention (hereinafter also noted as "this embodiment") will be described below on the basis of the drawings. However, this embodiment described below is only exemplification of the present invention in any point. Various improvements or modifications may be made without departing from the scope of the present invention. That is, when the present invention is to be put into practice, specific configuration according to the embodiment may be employed as appropriate.

Section 1. Configuration Example

First, a configuration example of a microneedle patch storage tool 1 according to this embodiment will be described by using FIG. 1. FIG. 1 is a perspective view exemplifying the microneedle patch storage tool 1 according to this embodiment. It should be noted that, in FIG. 1, for convenience of explanation, each direction is exemplified by using an x-axis, a y-axis, and a z-axis. Here, a z-axis direction corresponds to a direction perpendicular to the ground surface and a positive direction of the z-axis corresponds to the vertical upward. This z-axis direction corresponds to the "vertical direction" of the present invention. Moreover, an xy-plane corresponds to a plane horizontal to the ground surface, and an x-axis direction and a y-axis direction correspond to the direction horizontal to the ground surface, respectively. Hereinafter, the z-axis positive direction and negative direction are called an "upper" and a "lower", respectively, the x-axis positive direction and negative direction are called a "right" and a "left", respectively, and the y-axis positive direction and negative direction are called a "front" and a "rear", respectively. In FIG. 2 and after, each direction is called similarly.

As exemplified in FIG. 1, the microneedle patch storage tool 1 according to this embodiment is utilized for storing the microneedle patch 2 and comprises two pallets 10 stacked in the vertical direction. The two pallets 10 adjacent in the vertical direction are formed into the same shape and comprising 30 base parts 12 arranged by being aligned in five rows and six columns in front-and-rear and in right-and-left, respectively.

When the two base parts 12 faced with each other in the vertical direction of these two pallets 10 get close in the vertical direction, they constitute one patch holding part 11 holding one microneedle patch 2. That is, in this embodiment, when the two pallets 10 adjacent in the vertical direction are stacked, the 30 patch holding parts 11 arranged by being aligned in five rows by six columns in the front-and-rear and in right-and-left are constituted. Thus, in this embodiment, the microneedle patch storage tool 1 can store the 30 microneedle patches 2.

In each patch holding part 11, the microneedle patch 2 is placed on an upper surface of each base part 12 of the pallet 10 arranged on the lower side. A lower surface of each base part 12 of the pallet 10 arranged on the upper side covers the placed microneedle patch 2. As a result, the microneedle patch storage tool 1 can hold (store) the microneedle patch 2 in each of patch holding part 11. Hereinafter, configurations of the microneedle patch 2 to be stored and the pallet 10 constituting the microneedle patch storage tool 1 will be described in detail.

The pallet 10 arranged on the lower side corresponds to a "lower pallet" of the present invention, and the pallet 10 arranged on the upper side corresponds to an "upper pallet" of the present invention. However, in this embodiment, the correspondence relation is caused by the arrangement. That is, if the pallet 10 is arranged further below the pallet 10 arranged on the lower side, in the relation with the pallet 10 arranged further below, the pallet 10 arranged on the lower side functions as the upper pallet. Similarly, if the pallet 10 is arranged further above the pallet 10 arranged on the upper side, in the relation with the pallet 10 arranged further above, the pallet 10 arranged on the upper side functions as the lower pallet.

[Microneedle Patch]

First, a configuration example of the microneedle patch 2 stored in the microneedle patch storage tool 1 will be described. As exemplified in FIG. 1, the microneedle patch 2 stored in the microneedle patch storage tool 1 according to this embodiment is formed into a substantially oval shape. This microneedle patch 2 comprises a needle forming surface 21 on which a plurality of microneedles are formed, and a peripheral edge part 22 provided so as to surround a periphery of the needle forming surface 21.

The needle forming surface 21 is formed into a substantially circular shape. Each microneedle on this needle forming surface 21 is of a non-soluble type and is formed of biodegradable polymer such as PGA and PLA, for example. Moreover, each microneedle may be formed by a polymer which is not biodegradable such as nylon, polyethylene terephthalate and various engineering plastic, for example.

In this embodiment, each microneedle is arranged regularly or irregularly, and the medicament is applied on a tip end portion of each microneedle. Each microneedle has the medicament held on the tip end portion thereof and administered into the skin, and the medicament is delivered into the body. The medicament applied on each microneedle can be selected as appropriate in accordance with the embodiment.

Here, the medicament can contain all the compounds which act on the skin or permeate the skin and generate some useful action. Examples of the medicament suitable for such a purpose include bioactive peptides and derivatives thereof, nucleic acid, oligonucleotide, various antigenic proteins, bacteria, virus fragment and the like.

The aforementioned bioactive peptides and derivatives thereof include calcitonin, adrenocorticotropic hormone, parathyroid hormone (PTH), hPTH (1->34), insulin, somatotropin hormone, somatotropin hormone releasing hormone, bradykinin, substance P, dynorphin, thyroid stimulating hormone, prolactin, interferon, interleukin, G-CSF, glutathione peroxidase, superoxide dismutase, desmopressin, somatomedin, endothelin, and salts thereof and the like. The antigenic proteins include influenza antigen, HBs surface antigen, HBe antigen and the like.

It should be noted that, when a medicament solution is applied on the tip end of each microneedle so as to load the medicament in the microneedle tip end, it is desirable that a coexisting substance is dissolved in an aqueous solution of the medicament, and the medicament adheres to each microneedle with the coexisting substance in drying after application. For the coexisting substance, a substance not impairing stability of the medicament is used. Such coexisting substances can include water-soluble polymer substances such as hyaluronic acid, collagen, dextrin, dextran, chondroitin, hydroxypropylcellulose, ethylcellulose and the like, low molecular saccharides such as glucose, sucrose, maltose, trehalose and the like, and mixtures thereof, for example. Moreover, when the medicament solution is applied on the tip end of each microneedle so as to load the medicament in the microneedle tip end, an oxidization inhibitor, a surfactant and the like may be made to further coexist as necessary.

On the other hand, the microneedle is not formed on the peripheral edge part 22 arranged in the periphery of the needle forming surface 21. Thus, by providing this peripheral edge part 22, the microneedle patch 2 can be held without touching particularly the tip end portion of the microneedle on which the medicament is applied.

Such microneedle patch 2 can be manufactured by injection molding of a resin material such as plastic, excluding a portion of the microneedle formed of a biodegradable polymer. For example, a short diameter (the y-axis direction) of the microneedle patch 2 may be set within a range from 4 mm to 20 mm, and a long diameter (the x-axis direction) may be set within a range from 6 mm to 30 mm. Moreover, the thickness (the z-axis direction) of the microneedle patch 2 including the height of the microneedle may be set within a range from 0.3 mm to 1.5 mm.

However, the shape, the size, and the manufacturing method of the microneedle patch 2, the medicament to be applied and the configuration may not be limited to such examples and may be selected as appropriate in accordance with the embodiment. For example, the microneedle patch 2 may be formed into a shape such as a circle, a regular square, a rectangle or the like other than the oval.

[Pallet]

Subsequently, a configuration example of the pallet 10 constituting the microneedle patch storage tool 1 will be described by further using FIGS. 2 to 7. FIG. 2 is a perspective view exemplifying the pallet 10 according to this embodiment. FIG. 3 is a rear perspective view exemplifying the pallet 10 according to this embodiment. FIG. 4 is a plan view exemplifying the pallet 10 according to this embodiment. FIG. 5 is a bottom view exemplifying the pallet 10 according to this embodiment. FIG. 6 is an enlarged view of an A-B part in FIG. 4. FIG. 7 is an enlarged view of a C-D part in FIG. 5.

As exemplified in FIGS. 2 to 5, the pallet 10 has a substantially rectangular frame body 16 in this embodiment, and in this frame body 16, the 30 base parts 12 are arranged by being aligned in five rows by six columns in front-and-rear and in right-and-left. Each base part 12 is formed into a substantially oval frame shape by providing an opening 121 penetrating in the vertical direction at a center.

The opening 121 can be configured substantially equal to or slightly larger than the needle forming surface 21. It should be noted that, in this embodiment, the opening 121 is formed into a substantially circular shape, and the shape of the opening 121 corresponds to the shape of the needle forming surface 21. However, such an example is not limiting, and the shape of the opening 121 may have nothing to do with the shape of the needle forming surface 21.

Each base part 12 is coupled to the adjacent base part 12 or the frame body 16 by a coupling part 122 having a square columnar shape and a small width. Specifically, the four base parts 12 arranged at four corners of the frame body 16 are coupled to the frame body 16 by the three coupling parts 122, respectively, and are coupled to the adjacent base parts 12 by the two coupling parts 122, respectively. Moreover, the other base parts 12 adjacent to the frame body 16 are coupled to the frame body 16 by the one coupling part 122 and are coupled to the adjacent base parts 12 by the three coupling parts 122, respectively. Further, the base part 12 not adjacent to the frame body 16 is adjacent to the other base parts 12 in the front-and-rear direction (the y-axis direction in the figure) and in the right-and-left direction (the x-axis direction in the figure), respectively, and is coupled to the base parts 12 adjacent in the front-and-rear and in the right-and-left by the four coupling parts 122, respectively. As a result, the 30 base parts 12 are made in a series in the frame body 16 in five rows by six columns in the front-and-rear direction and in the right-and-left direction.

In other words, regarding each coupling part 122 coupling each base part 12 and the frame body 16, each coupling part 122 arranged on the outermost side in the plane direction and constituting an outer peripheral part extends partially in the vertical direction along an inner peripheral surface of the frame body 16. Thus, when the two pallets 10 adjacent in the vertical direction are stacked, the outer peripheral part constituting each coupling part 122 of the pallet 10 arranged on the lower side can be fitted in the inner side of the frame body 16 of the pallet 10 arranged on the upper side. As a result, in this embodiment, when the two pallets 10 adjacent in the vertical direction are stacked, these two pallets 10 can be prevented from being separated easily.

Moreover, as exemplified in FIGS. 2, 4, and 6, in this embodiment, six lower protrusions 13 supporting the peripheral edge part 22 of the microneedle patch 2 from below are arranged on an upper surface of each base part 12 in circumferentially divided manner. These six lower protrusions 13 may be arranged at an equal interval or do not have to be arranged at the equal interval. The arrangement of the lower protrusions 13 can be selected as appropriate in accordance with the embodiment.

In this embodiment, the four lower protrusions 13 in front and rear in these six lower protrusions 13 are formed into substantially square columnar shapes. On the other hand, the two lower protrusions 13 at the center in the front-and-rear direction are formed into substantially columnar shapes. These two lower protrusions 13 are provided close to the coupling part 122 to be coupled to the base parts 12 adjacent in the right-and-left direction or the frame body 16.

In addition, in this embodiment, four side wall pieces 14 are provided separately on the upper surface of each base part 12. The four side wall pieces 14 are formed into substantially flat-plate shapes and are arranged in circumferentially divided manner. Specifically, the four side wall pieces 14 are arranged so as to be adjacent to an outer side in the plane direction of the four lower protrusions 13 in the front-and-rear. The height of each side wall piece 14 (the length in the z-axis direction) is larger than the height of each lower protrusion 13 (the length in the z-axis direction).

Moreover, as exemplified in FIGS. 3, 5, and 7, in this embodiment, the eight upper protrusions 15 pressing the peripheral edge part 22 of the microneedle patch 2 from the upper side are arranged in circumferentially divided manner on the lower surface of the base part 12. These eight upper protrusions 15 may be arranged at an equal interval or do not have to be arranged at the equal interval. The arrangement of the upper protrusions 15 can be selected as appropriate in accordance with the embodiment. Moreover, the arrangement of the upper protrusions 15 may correspond to or does not have to correspond to the arrangement of the lower protrusions 13.

In this embodiment, the four upper protrusions 15 arranged at the center in the front-and-rear direction and at the center in the right-and-left direction in these eight upper protrusions 15 are formed into substantially square columnar shapes. On the other hand, the other four upper protrusions 15 are formed into substantially columnar shapes. Moreover, the two upper protrusions 15 at the center in the front-and-rear direction are provided close to the coupling part 122 to be coupled to the base parts 12 adjacent in the right-and-left direction or the frame body 16.

In addition, a partition piece 123 extending downward is provided on the lower surface of the coupling part 122. The partition piece 123 is formed into a flat plate shape and is arranged so as to be adjacent to the two upper protrusions 15 provided close to both right and left sides of the coupling part 122. It should be noted that the height of each partition piece 123 (the length in the z-axis direction) is higher than the height of each upper protrusion 15 (the length in the z-axis direction).

Moreover, as exemplified in FIGS. 2 to 5, in this embodiment, two plane regions 17 are provided in a region at the center in the right-and-left direction on both end portions in the front-and-rear direction so as to fill a gap between the two base parts 12 adjacent in the right-and-left direction and the frame body 16, respectively. An insertion hole 19 penetrating in the vertical direction is provided in the plane region 17 on a front side in these two plane regions 17. Moreover, below this insertion hole 19, a projection 18 for positioning is provided.

Since this projection 18 is coupled to the inner peripheral surface of the frame body 16, and it is formed into an L-shape, it has a portion extending in the vertical direction below the insertion hole 19. This projection 18 is formed into a columnar shape, and the insertion hole 19 is formed into a cylindrical shape corresponding to that. An inner diameter of the insertion hole 19 is larger than an outer diameter of the projection 18 so that the insertion hole 19 can accept the projection 18 of another pallet 10.

The pallet 10 as described above can be manufactured by injection molding of a resin material such as plastic. However, as will be described later, the pallet 10 is likely to be in contact with the washing liquid such as water, ethanol and the like in washing of the microneedle. Moreover, the pallet 10 holds the microneedle patch 2 in point contact by the lower protrusion 13 and the upper protrusion 15. Thus, it is preferable that the material of the pallet 10 is water-proof so that it can be in contact with the washing liquid and has high mechanical strength so that it can hold the microneedle patch 2 appropriately. Moreover, it is preferable that the material of the pallet 10 is less deformable by the temperature change after injection molding. From these viewpoints, the material of the pallet 10 is preferably polyethylene terephthalate, polycarbonate, nylon-6, nylon-66 and the like. Moreover, engineering plastic may be used as the material of the pallet 10.

Section 2. Usage

Subsequently, one example of a method of storing the microneedle patch 2 in the microneedle patch storage tool 1 according to this embodiment will be described by using FIGS. 8 to 11. FIG. 8 is an enlarged view of the A-B part exemplifying a state where the microneedle patch 2 is held. FIG. 9 is an enlarged view of the C-D part exemplifying the state where the microneedle patch 2 is held. FIG. 10 is a sectional view related to a line E in FIGS. 4 and 5, exemplifying the state where the microneedle patch 2 is held. FIG. 11 is a sectional view related to a line F in FIGS. 4 and 5, exemplifying the state where the microneedle patch 2 is held.

First, a plurality of the pallets 10 for constituting the microneedle patch storage tool 1 is prepared. When the microneedle patch storage tool 1 is to be constituted with the two pallets 10, two the pallets 10 are prepared. A case where the microneedle patch storage tool 1 is constituted with the two pallets 10 will be described below in order to facilitate the explanation.

Subsequently, the microneedle patch 2 is placed automatically or manually on each base part 12 of one of the prepared two pallets 10. At this time, as exemplified in FIG. 8, each lower protrusion 13 provided on the upper surface of each base part 12 supports the peripheral edge part 22 of the microneedle patch 2. Moreover, the four side wall pieces 14 are adjacent to such lower protrusions 13 on an outer side in the plane direction and thus, they surround the outer periphery of the microneedle patch 2. Thus, in this step, a place on which the microneedle patch 2 is to be placed can be aligned on the basis of these four side wall pieces 14. It should be noted that there can be the base part 12 on which the microneedle patch 2 is not placed.

Then, on the one pallet 10 on which the one or a plurality of microneedle patches 2 are placed, the other pallet 10 is stacked. At this time, the both pallets 10 can be aligned by the insertion hole 19 of the one pallet 10 and the projection 18 of the other pallet 10. That is, by adjusting the positions of the both pallets 10 so that the insertion hole 19 of the one pallet 10 arranged on the lower side accepts the projection 18 of the other pallet 10 arranged on the upper side, the both pallets 10 can be aligned.

By carrying out the alignment as above, each base part 12 of the one pallet 10 and each base part 12 of the other pallet 10 are faced with each other in the vertical direction. And when the other pallet 10 is stacked on the one pallet 10, as exemplified in FIG. 9, each upper protrusion 15 provided on the lower surface of each base part 12 of the other pallet 10 arranged on the upper side presses the peripheral edge part 22 of the microneedle patch 2. As a result, the two base parts 12 faced with each other in the vertical direction of the two pallets 10 are brought close to each other and constitute the patch holding part 11 holding the microneedle patch 2.

Specifically, in the state exemplified in FIGS. 10 and 11, each patch holding part 11 holds (stores) the microneedle patch 2. That is, each patch holding part 11 sandwiches the peripheral edge part 22 of the microneedle patch 2 in the vertical direction substantially in point contact by the eight upper protrusions 15 on the pallet 10 arranged on the upper side and the six lower protrusions 13 of the pallet 10 arranged on the lower side. As a result, each patch holding part 11 holds (stores) the microneedle patch 2.

At this time, the opening 121 penetrating in the vertical diction is provided in the both base parts 12 faced with each other in the vertical direction. Thus, in this embodiment, each patch holding part 11 is opened to both upper and lower directions. That is, in this embodiment, an access can be made to the microneedle patch 2 held in each patch holding part 11 through the both openings 121 arranged in the vertical direction.

Moreover, the two adjacent patch holding parts 11 are coupled by the coupling part 122, and the partition piece 123 partitioning the two adjacent patch holding parts 11 is provided on the lower surface of each coupling part 122. As partially exemplified in FIG. 11, the partition piece 123 extending downward from the coupling part 122 of the pallet 10 arranged on the upper side is arranged so as to be fitted between the two lower protrusions 13 provided close to the both ends of the corresponding coupling part 122 of the pallet 10 arranged on the lower side.

Thus, the partition piece 123 can prevent displacement of the microneedle patch 2 similarly to the side wall piece 14. Specifically, in the patch holding part 11 according to this embodiment, the four partition pieces 123 are arranged in the front-and-rear and in the right-and-left of the microneedle patch 2, and these four partition pieces 123 surround the outer periphery of the microneedle patch 2. As a result, these four partition pieces 123 can prevent the displacement of the microneedle patch 2.

On the line E exemplified in FIG. 10, the arrangement of the upper protrusions 15 corresponds to the arrangement of the lower protrusions 13 in the vertical direction. On the other hand, on the line F exemplified in FIG. 11, the arrangement of the upper protrusions 15 does not correspond to the arrangement of the lower protrusions 13 in the vertical direction. As described above, the arrangement of the upper protrusions 15 may correspond to or does not have to correspond to the arrangement of the lower protrusions 13. Each of the upper protrusions 15 and each of the lower protrusions 13 may be arranged as appropriate so that the microneedle patch 2 can be held stably.

As described above, the microneedle patch storage tool 1 storing the microneedle patch 2 can be constituted with the two pallets 10. It should be noted that, in the aforementioned usage, the example in which the microneedle patch storage tool 1 is constituted with the two pallets 10 was described. However, the number of the pallets 10 constituting the microneedle patch storage tool 1 is not limited to two but may be three or more.

A case where the microneedle patch storage tool 1 is constituted with three or more pallets 10 can be also described similarly to the case of constitution of the microneedle patch storage tool 1 by the two pallets 10. That is, by repeating the step of placing the microneedle patch 2 and the step of stacking another pallet 10 on the pallet 10 on which the microneedle patch 2 is placed, the microneedle patch storage tool 1 can be constituted with three or more pallets 10.

[Action/Effect]

As described above, in the microneedle patch storage tool 1 according to this embodiment, the peripheral edge part 22 of the microneedle patch 2 is sandwiched substantially in point contact by the upper protrusions 15 of the pallet 10 on the upper side and the lower protrusions 13 on the pallet 10 on the lower side. Thus, when the microneedle patch 2 is to be stored in the microneedle patch storage tool 1, the microneedle formed on the needle forming surface 21 provided on the inner-plane side from the peripheral edge part 22 can be prevented from being damaged.

Moreover, in this embodiment, the opening 121 penetrating in the vertical direction is provided in the both base parts 12 faced with each other in the vertical direction, and each patch holding part 11 holding the microneedle patch 2 is opened to the both upper and lower directions. Thus, even after the microneedle patch 2 is stored in the microneedle patch storage tool 1, an access can be made to the microneedle patch 2 from the outside through each opening 121 which is substantially equal to or slightly larger than the needle forming surface 21.

Therefore, even in the state where the microneedle patch 2 is stored in the microneedle patch storage tool 1, the washing of the microneedle and the application of the medicament can be carried out easily. The washing step of the microneedle can be carried out in a step as described below, for example. That is, the washing liquid such as water, ethanol and the like is injected toward the microneedle patch 2 through each opening 121. Alternatively, the microneedle patch 2 is made to sink together with the microneedle patch storage tool 1 in the washing liquid filled in a container or the like. At this time, in this embodiment, the four side wall pieces 14 surrounding the outer periphery of the microneedle patch 2 are separated from each other, and each patch holding part 11 is partially opened to the plane direction. Thus, by causing the microneedle patch storage tool 1 to sink in the washing liquid, the washing liquid flows into each patch holding part 11 through each opening 121 and between the side wall pieces 14. As a result, the washing step of the microneedle can be carried out.

Moreover, the step of applying the medicament on the tip end portion of the microneedle can be carried out in a step as described below, for example. That is, the medicament is applied on the microneedle formed on the needle forming surface 21 through the opening 121 in the direction to which the needle forming surface 21 is directed. In this embodiment, since the needle forming surface 21 is directed to the upper direction, the medicament is applied on the microneedle formed on the needle forming surface 21 through each opening 121 in the pallet 10 arranged on the upper side. As a result, the step of applying the medicament on the tip end portion of the microneedle can be carried out.

Thus, according to this embodiment, without taking out the microneedle patch 2 from the microneedle patch storage tool 1, the washing of the microneedle and the application of the medicament can be carried out easily. Thus, according to this embodiment, the work cost for the washing of the microneedle and the application of the medicament can be suppressed. Moreover, according to this embodiment, the washing of the microneedle and the application of the medicament can be carried out in an easy step as described above.

It should be noted that the washing liquid having been injected or flowed into each patch holding part 11 can be discharged to the outside of each patch holding part 11 through each opening 121 and between the side wall pieces 14. Moreover, after the microneedle patch 2 is washed, when the microneedle patch 2 is to be dried, air can be made to flow through each opening 121 and between the side wall pieces 14. Thus, after the microneedle patch 2 is washed, the microneedle patch 2 can be dried rapidly. That is, according to this embodiment, the time for the step of washing and drying of the microneedle can be made relatively shorter.

Moreover, in this embodiment, the place on which the microneedle patch 2 is to be placed can be aligned by the four side wall pieces 14. Furthermore, after the microneedle patch 2 is stored in each patch holding part 11, the displacement of the microneedle patch 2 can be prevented by the four side wall pieces 14 and the four partition pieces 123. Thus, according to this embodiment, the microneedle patch 2 can be held stably in each patch holding part 11.

Moreover, in this embodiment, each of the patch holding parts 11 is arrayed by being aligned in the front-and-rear and in the right-and-left. Thus, the procedure such as the application of the medicament on the microneedle patch 2 or the like can be carried out relatively easily. Thus, according to this embodiment, the step of applying the medicament on the tip end portion of each microneedle and the like can be carried out rapidly, whereby the work time for the procedure for the microneedle patch 2 can be made relatively shorter.

Moreover, in this embodiment, the two pallets 10 constituting the microneedle patch storage tool 1 are formed in the same shape. Thus, according to this embodiment, there is no need to manufacture the pallets 10 having a plurality of shapes and thus, a manufacturing cost of the microneedle patch storage tool 1 can be suppressed.

Moreover, in this embodiment, the both pallets 10 can be aligned by the projection 18 for positioning and the insertion hole 19. Thus, the both pallets 10 can be stacked easily, and after the both pallets 10 are stacked, each pallet 10 can be prevented from being displaced. Therefore, according to this embodiment, the step of stacking two or more pallets 10 can be facilitated, and collapse of the plurality of stacked pallets 10 can be prevented.

Moreover, in this embodiment, when each pallet 10 storing each microneedle patch 2 and stacked is to be washed and sterilized by water, ethanol and the like, each microneedle patch 2 is supported in point contact by each pallet 10 from upper and lower and right and left. Thus, even if a physical impact occurs in each pallet 10 due to vibration, falling, rolling or the like, the impact is prevented from being transmitted directly to the needle of each microneedle patch 2, whereby the needle of each microneedle patch 2 can be prevented from being damaged.

Section 3. Variation

The embodiment of the present invention has been described, but the aforementioned description is merely exemplification of the present invention in any point. It is needless to say that various improvements or variations without departing from the scope of the present invention can be made. Moreover, regarding each constituent element of the microneedle patch storage tool 1, omission, replacement and addition of the constituent element may be made as appropriate in accordance with the embodiment. The shape and the size of each constituent element of the microneedle patch storage tool 1 may be set as appropriate in accordance with the embodiment. Furthermore, the material of each constituent element of the microneedle patch storage tool 1 may be selected as appropriate in accordance with the embodiment. For example, the following changes are possible. It should be noted that, in the variations described below, the similar reference numerals are used for the constituent elements similar to those in the aforementioned embodiment, and the explanation is omitted as appropriate.

<3.1>

For example, in the aforementioned embodiment, the base part 12 constituting the patch holding part 11 is formed into a substantially oval shape. However, the shape of the base part 12 is not limited to such an example but may be selected as appropriate in accordance with the embodiment. For example, the base part 12 may be formed into shapes as exemplified in FIGS. 12 and 13.

FIGS. 12 and 13 are perspective views exemplifying a pallet 10A and a pallet 10B according to this variation. The pallet 10A has the configuration similar to that of the pallet 10 except that a base part 12A is formed into a substantially regular square shape. Moreover, the pallet 10B has the configuration similar to that of the pallet 10 except that a base part 12B is formed into a substantially circular shape. As described above, the base part 12 may be formed into a regular square shape or a circular shape. Moreover, the base part 12 may be formed into a shape other than them.

<3.2>

Moreover, for example, in the aforementioned embodiment, each patch holding part 11 is opened to both upper and lower directions due to the opening 121 provided on the both sides in the vertical direction. However, it is only necessary that each patch holding part 11 is opened to at least either one of the upper and lower directions, and either one of the openings 121 provided on the both sides in the vertical direction may be omitted. That is, either one of the two base parts 12 constituting each patch holding part 11 may be formed into a flat plate shape without the opening 121 instead of a frame shape. It is only necessary that the patch holding part 11 is opened to at least either one of the upper and lower directions so that the washing of the microneedle provided in the stored microneedle patch 2 and the medicament application on the tip end portion of the microneedle can be carried out.

<3.3>

Moreover, for example, in the aforementioned embodiment, the four side wall pieces 14 are provided separately on the upper surface of each base part 12. However, the constitution of the side wall pieces 14 is not limited to such an example but may be selected as appropriate in accordance with the embodiment. For example, the side wall pieces 14 may be formed integrally, whereby the side wall piece 14 may be configured so as to completely cover the outer periphery of the microneedle patch 2. Moreover, the number of side wall pieces 14 provided on the upper surface of each base part 12 is not limited to four but may be any of one to three or five or more. The number of side wall pieces 14 provided on the upper surface of each base part 12 can be selected as appropriate in accordance with the embodiment.

Moreover, as exemplified in FIG. 14, each side wall piece 14 may be omitted. FIG. 14 is a perspective view exemplifying a pallet 10C according to the variation. In the pallet 10C exemplified in FIG. 14, 100 base parts 12C are arranged by being aligned in ten rows by ten columns in the front-and-rear and in the right-and-left. The side wall piece 14 is not provided on each base part 12C, but only the lower protrusion 13 is provided. Even with such pallet 10C, the microneedle patch 2 can be sandwiched by the plurality of lower protrusions 13 and the plurality of upper protrusions 15. That is, the microneedle patch storage tool can be constituted by stacking the plurality of pallets 10C in the vertical direction.

Moreover, in the aforementioned embodiment, for example, each side wall piece 14 is provided on the upper surface of each base part 12. However, the place where each side wall piece 14 is provided is not limited to such an example but may be selected as appropriate in accordance with the embodiment as long as the side wall pieces 14 are arranged in circumferentially divided manner so as to surround the outer periphery of the microneedle patch 2. For example, at least a part of the side wall pieces 14 may be provided on the lower surface of each base part 12.

<3.4>

Moreover, in the aforementioned embodiment, each patch holding part 11 is coupled to the adjacent patch holding part 11 by the coupling part 122, and on each coupling part 122, the partition piece 123 partitioning the two adjacent patch holding parts 11 is provided. However, a form of the patch holding part 11 is not limited to such an example but may be selected as appropriate in accordance with the embodiment. For example, each coupling part 122 and each partition piece 123 may be omitted. In this case, the adjacent base parts 12 may be coupled directly to each other. Moreover, each partition piece 123 may be provided not on the lower surface of the coupling part 122 but on the upper surface of the coupling part 122.

Moreover, in the aforementioned embodiment, the projection 18 and the insertion hole 19 are positioned so that the projection 18 for positioning of the pallet 10 arranged on the upper side is inserted into the insertion hole 19 of the pallet 10 arranged on the lower side. However, the position relation between the projection 18 and the insertion hole 19 is not limited to such an example but may be opposite. That is, the projection 18 and the insertion hole 19 may be positioned so that the projection 18 of the pallet 10 arranged on the lower side is inserted into the insertion hole 19 of the pallet 10 arranged on the upper side. It is only necessary that the projection 18 is provided on either one of the two adjacent pallets 10 and the insertion hole 19 is provided in the other. Moreover, the projection 18 and the insertion hole 19 may be omitted.

<3.5>

Moreover, for example, in the aforementioned embodiment, the base parts 12 of the pallet 10 are provided at 30 spots. That is, in the microneedle patch storage tool 1 according to the aforementioned embodiment, the 30 patch holding parts 11 are formed, and the 30 microneedle patches 2 can be stored. However, the number of the patch holding parts 11 provided in the microneedle patch storage tool 1, in other words, the number of the stored microneedle patches 2 is not limited to such an example but may be selected as appropriate in accordance with the embodiment. For example, the number of the patch holding parts 11 may be one or 2 to 29 or 31 or more. It should be noted that the number of patch holding parts 11 provided between the two adjacent pallets 10 is preferably 9 to 150 from the viewpoint of the size and handling of each pallet 10.

Moreover, in this embodiment, for example, the base parts 12 of the pallet 10 are aligned in five rows and six columns in the front-and-rear and in the right-and-left. That is, in the microneedle patch storage tool 1 according to the aforementioned embodiment, the plurality of patch holding parts 11 are aligned in the front-and-rear and in the right-and-left. However, the arrangement of each patch holding part 11 is not limited to such an example but may be selected as appropriate in accordance with the embodiment. For example, the patch holding parts 11 do not have to be aligned in the front-and-rear and in the right-and-left.

Moreover, in the aforementioned embodiment, for example, the six lower protrusions 13 are provided on the upper surface of each base part 12. However, the number of the lower protrusions 13 provided on the upper surface of each base part 12 is not limited to such an example but may be selected as appropriate in accordance with the embodiment. It is only necessary that the lower protrusions 13 may be plural. That is, the number of the lower protrusions 13 provided on the upper surface of each base part 12 may be two to five or seven or more. Moreover, the numbers of lower protrusions 13 to be provided may be different among the base parts 12 different from each other. Furthermore, the shape of each lower protrusion 13 may be selected as appropriate in accordance with the embodiment. The shapes of the plurality of lower protrusions 13 provided on the one base part 12 may be different from each other.

Similarly, in the aforementioned embodiment, the eight upper protrusions 15 are provided on the lower surface of each base part 12. However, the number of the upper protrusions 15 provided on the lower surface of each base part 12 is not limited to such an example but may be selected as appropriate in accordance with the embodiment. It is only necessary that the upper protrusions 15 are plural. That is, the number of the upper protrusions 15 provided on the lower surface of each base part 12 may be two to seven or nine or more. Moreover, the numbers of upper protrusions 15 to be provided may be different among the base parts 12 different from each other. Furthermore, the shape of each upper protrusion 15 may be selected as appropriate in accordance with the embodiment. The shapes of the plurality of upper protrusions 15 provided on the one base part 12 may be different from each other. It should be noted that the numbers of the lower protrusions 13 and the upper protrusions 15 are preferably three, four or six, respectively, from a viewpoint that the microneedle patch 2 is held properly and accessibility from the outside is not impaired.

<3.6>

Moreover, in the aforementioned embodiment, for example, the microneedle patch storage tool 1 is constituted with the two pallets 10. However, the number of the pallets 10 constituting the microneedle patch storage tool 1 is not limited to two but may be three or more. Moreover, each pallet 10 may be used as a single body as the upper pallet or the lower pallet.

Moreover, in the aforementioned embodiment, for example, each pallet 10 constituting the microneedle patch storage tool 1 is formed into the same shape. However, the shape of each pallet 10 is not limited to such an example but each pallet 10 does not have to be formed into the same shape.

For example, on either one of the upper and lower pallets 10, each base part 12 may be formed not having the frame shape but having the flat plate shape as described above and does not have to comprise the opening 121. In this case, each pallet 10 is not formed into the same shape but the patch holding part 11 is opened to either one of the upper and lower. Specifically, the patch holding part 11 is not opened to the base part 12 side on which the opening 121 is not provided (either one of the upper and lower) but opened on the base part 12 side on which the opening 121 is provided (the other). As described above, each pallet 10 does not have to be formed into the same shape.

<3.7>

Moreover, for example, in the aforementioned embodiment, the microneedle patch 2 is stored in the microneedle patch storage tool 1 (patch holding part 11) so that the needle forming surface 21 is directed to the upper direction. However, the direction of the microneedle patch 2 in storage is not limited to such an example. The microneedle patch 2 may be stored in the microneedle patch storage tool 1 so that the needle forming surface 21 is directed to the lower direction, that is, so that the needle forming surface 21 is directed to the base part 12 side of the pallet 10 arranged on the lower side.

Moreover, the microneedle patch storage tool 1 according to the aforementioned embodiment may be used with being inverted in the vertical direction. That is, each pallet 10 of the microneedle patch storage tool 1 may be used so that the upper surface of each base part 12 is directed to the lower direction. Even if the upper and lower directions of each pallet 10 are switched, the microneedle patch 2 can be stored in the microneedle patch storage tool 1 similarly to the aforementioned embodiment.

REFERENCE NUMERALS

1 microneedle patch storage tool
10 pallet
11 patch holding part
12 base part
121 opening
122 coupling part
123 partition piece
13 lower protrusion
14 side wall piece
15 upper protrusion
16 frame body
17 plane region
18 projection (for positioning)
19 insertion hole
2 microneedle patch
21 needle forming surface
22 peripheral edge part

The invention claimed is:

1. A microneedle patch storage tool configured to hold a microneedle patch, the microneedle patch storage tool comprising
   a plurality of pallets stacked in a vertical direction,
   wherein pallets adjacent in the vertical direction among the plurality of pallets constitute one or a plurality of patch holding parts configured to hold the microneedle patch,
   wherein the patch holding part comprises a first base part and a second base part that are arranged in the vertical direction,
   wherein the first base part comprises;
      a first opening having a shape configured to be corresponding to a needle forming surface of a microneedle patch which the microneedle patch storage tool is intended to hold, and
      a plurality of first protrusions arranged in circumferentially divided manner around the first opening,
   wherein the second base part comprises;
      a second opening having a shape configured to be corresponding to the needle forming surface of the microneedle patch which the microneedle patch storage tool is intended to hold, and
      a plurality of second protrusions arranged in circumferentially divided manner around the second opening, and
   wherein the plurality of first protrusions and the plurality of second protrusions are configured to sandwich a peripheral edge part of the microneedle patch which the microneedle patch storage tool is intended to hold, in the vertical direction, and
   wherein for each patch holding part, a plurality of side wall pieces are provided radially outward of the first protrusions and are arranged separately from each other and in circumferentially divided manner to surround the same first opening surrounded by the first protrusions, the side wall piece has a larger height than the first protrusion, and the second protrusions are positioned to be corresponding to the first protrusions.

2. The microneedle patch storage tool according to claim 1, wherein
   the two adjacent patch holding parts are coupled by a coupling part, and
   a partition piece for partitioning the two adjacent patch holding parts is provided on the coupling part.

3. The microneedle patch storage tool according to claim 2, wherein the plurality of patch holding parts are arranged by being aligned in front-and-rear and in right-and-left.

4. The microneedle patch storage tool according to claim 1, wherein the plurality of pallets are formed into the same shape.

5. The microneedle patch storage tool according to claim 1, wherein
   a projection for positioning is provided on one of the two adjacent pallets, and
   an insertion hole for accepting the projection is provided in the other pallet.

6. A system, comprising:
   a lower pallet, and
   a microneedle patch, wherein the lower pallet comprises one or a plurality of base parts on each of which the microneedle patch is placed, the base part is formed into a frame shape by providing an opening penetrating in the vertical direction at a center, wherein the opening has a shape corresponding to a needle forming surface of the microneedle patch, and on an upper surface of the base part, a plurality of lower protrusions supporting a peripheral edge part of the microneedle patch from a lower side is arranged in circumferentially divided manner around the opening, wherein each base part further comprises a plurality of side wall pieces arranged radially outward of the lower protrusions and arranged separately from each other and in circumferentially divided manner on the upper surface of the base part to surround the same opening surrounded by the lower protrusions, and the side wall piece has a larger height than the lower protrusion.

7. A system, comprising:

an upper pallet; and a microneedle patch, wherein the upper pallet comprises one or a plurality of base parts covering the microneedle patch, the base part is formed into a frame shape by providing an opening penetrating in the vertical direction at a center, wherein the opening has a shape corresponding to a needle forming surface of the microneedle patch, and on a lower surface of the base part, a plurality of upper protrusions pressing a peripheral edge part of the microneedle patch from an upper side is arranged in circumferentially divided manner around the opening, wherein each base part further comprises, on an upper surface of the base part, a plurality of lower protrusions and a plurality of side wall pieces arranged radially outward of the lower protrusions and arranged separately from each other and in circumferentially divided manner to surround the same opening surrounded by the lower protrusions, the side wall piece has a larger height than the lower protrusion, and the lower protrusions are positioned to be corresponding to the upper protrusions.

* * * * *